United States Patent [19]
Ogle

[11] 3,942,514
[45] Mar. 9, 1976

[54] ARTERIAL BLOOD SAMPLING DEVICE WITH INDICATOR

[75] Inventor: Robert W. Ogle, Newport Beach, Calif.

[73] Assignee: IMS Limited, S. El Monte, Calif.

[22] Filed: Feb. 28, 1974

[21] Appl. No.: 446,664

[52] U.S. Cl. ........ 128/2 F; 128/2.05 D; 128/2.05 E
[51] Int. Cl.² .......................................... A61B 5/00
[58] Field of Search .. 128/2 F, DIG. 5, 216, 2.05 D, 128/2.05 E, 220; 116/117 R, 117 C, 125, 114 R, DIG. 7, DIG. 8, 70; 73/421 R, 422 R, 389, 406

[56] References Cited
UNITED STATES PATENTS

| | | | |
|---|---|---|---|
| 2,866,453 | 12/1958 | Jewett | 128/2.05 D |
| 3,308,820 | 3/1967 | Hubbard | 128/216 |
| 3,376,866 | 4/1968 | Ogle | 128/220 |
| 3,675,722 | 7/1972 | Balmes, Sr. | 73/406 X |
| 3,703,879 | 11/1972 | Huthsing, Jr. | 73/406 X |
| 3,730,168 | 5/1973 | McWhorter | 128/2.05 D |
| 3,785,367 | 1/1974 | Fortin et al. | 128/2 F |

Primary Examiner—Robert W. Michell
Assistant Examiner—Henry S. Layton
Attorney, Agent, or Firm—Wills, Green & Mueth

[57] ABSTRACT

An arterial blood sampling device comprising a syringe adapted to receive an arterial blood sample, a fluid path extending from the syringe and terminating in a scarf which is adapted to be received in an artery. Pressure sensitive means are provided along the fluid path whereby the presence or absence of arterial blood pressure within the path can be visually detected.

8 Claims, 8 Drawing Figures

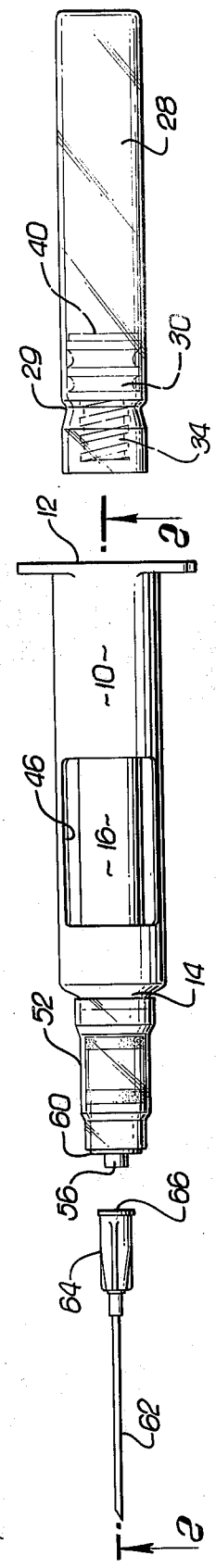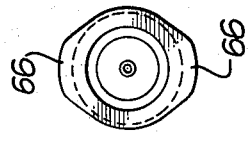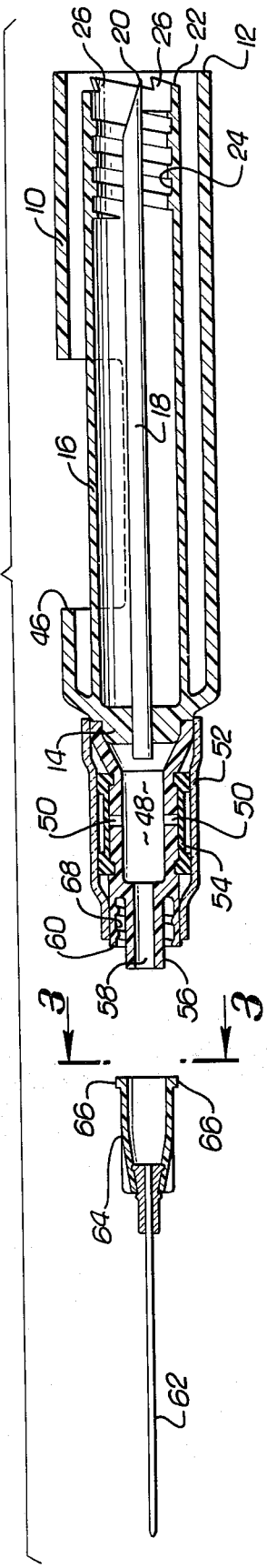

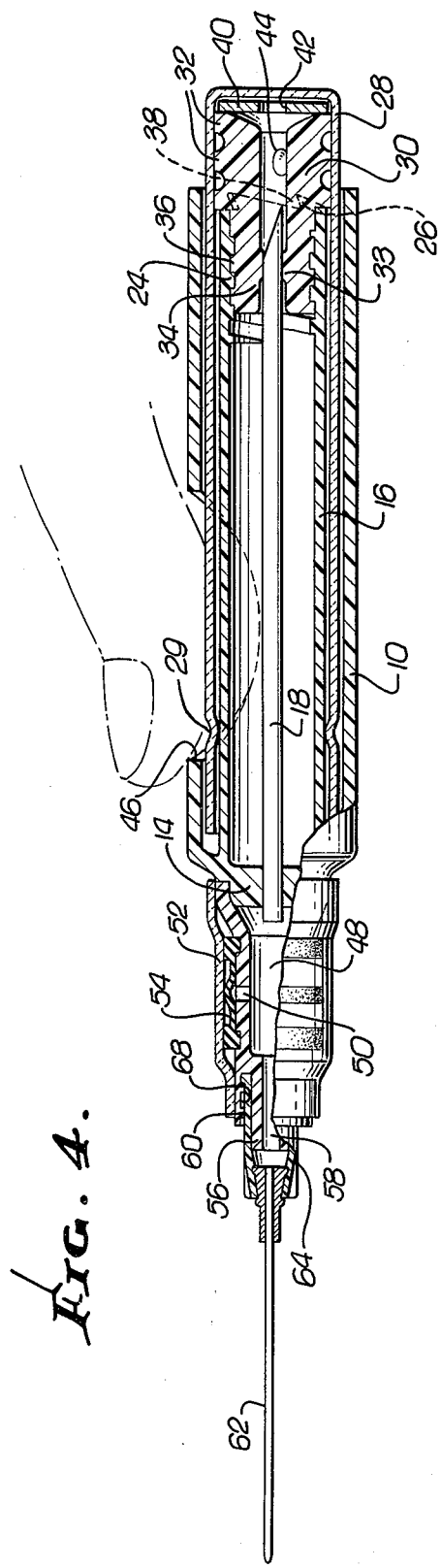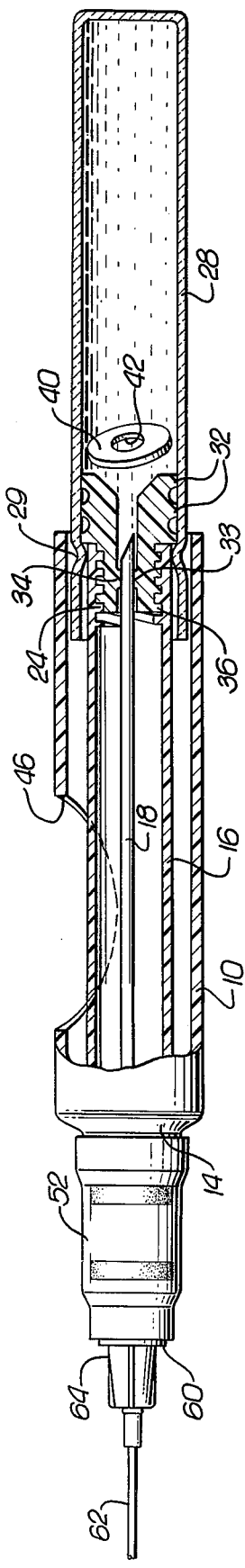

ARTERIAL BLOOD SAMPLING DEVICE WITH INDICATOR

BACKGROUND OF THE INVENTION

The taking of venous blood samples is quite well-known. The taking of arterial blood samples has also become recognized as important. In patients suffering from diseases of the lungs or heart, it is important to know the oxygen content of the blood. This content is determined by blood gas analysis of arterial blood. It is essential, therefore, that arterial blood, rather than venous blood be withdrawn for such analysis. Heretofore, such blood was obtained using a conventional hypodermic syringe. The problem is that it is difficult to tell whether the scarf of the needle is in an artery or a vein. Arteries are generally deep within the body tissue, making the determination by feel or sight difficult. This is particularly true in obese patients and infants. If the intended arterial blood sample is not arterial blood, another attempt must be made to the discomfort of the patient. Also, in certain types of cases, important time is lost in the diagnostic procedure.

The present invention provides a dependable way of taking arterial blood samples and it is believed that the device of this invention represents a major advance in the art. Its disadvantages and benefits will be evident to those skilled in the art.

SUMMARY OF THE INVENTION

Briefly, this invention comprises a novel and improved arterial blood sampling device comprising a syringe adapted to receive an arterial blood sample, a fluid path extending from said syringe and terminating in a scarf which is adapted to be received in an artery, means along said fluid path whereby the presence or absence of arterial blood pressure within said path can be visually detected, said means being non-responsive to venous blood pressure.

It is an object of this invention to provide a novel arterial blood sampling device.

More particular, it is an object of this invention to provide a novel blood sampling device which provides for a signaling mechanism which tells the nurse whether or not the scarf of the needle is in the artery of the patient.

It is a further object of the invention to provide a more fool proof arterial blood sampling device which the nurse, when otherwise preoccupied, cannot operate in such a manner that the blood sample is spilled.

A further object of the invention is an arterial blood sampling device which is provided with means for preventing unwanted clotting of the blood sample.

These and other objects and advantages of this invention will be apparent from the detailed description which follows, taken in conjunction with the accompanying drawings.

DESCRIPTION OF THE PREFERRED EMBODIMENTS

Turning to the drawings:

FIG. 1 is a side view of one embodiment of the invention in disassembled form.

FIG. 2 is a longitudinal sectional view of the device of FIG. 1 taken along the line 2—2.

FIG. 3 is a cross-sectional view of the device of FIG. 1 taken along the line 3—3 in FIG. 2.

FIG. 4 is a longitudinal sectional view of the device of FIGS. 1 through 3 in operation showing the deletion of arterial blood pressure.

FIG. 5 is a longitudinal sectional view of the device of FIGS. 1 through 4 after the arterial blood sample has been taken.

Figure 6:
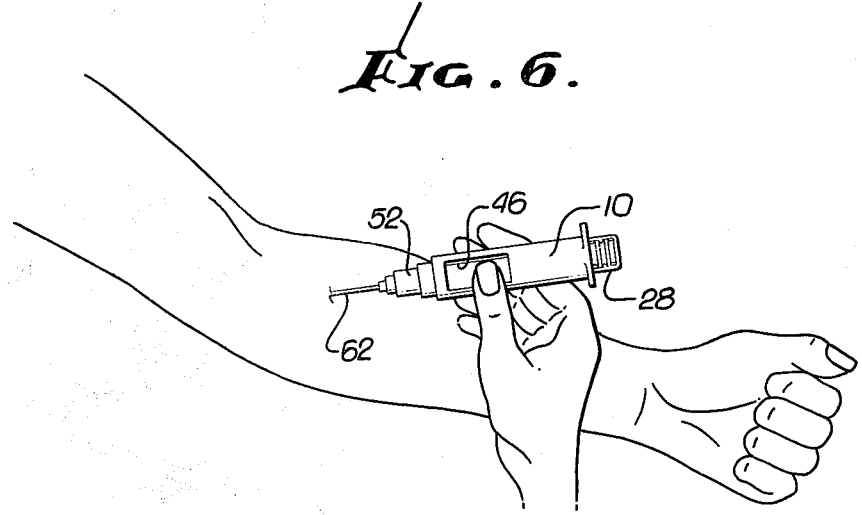
FIG. 6 is a perspective view showing the insertion of the device of FIGS. 1 through 5 into the patient.
Figure 7:
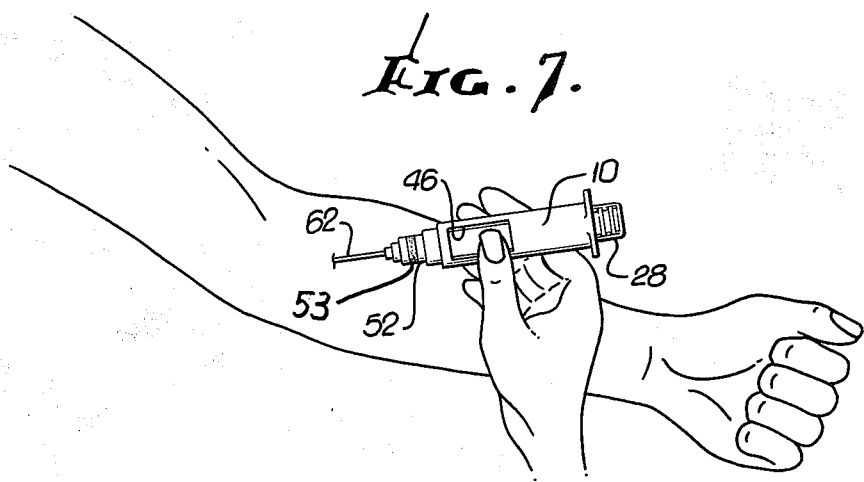
FIG. 7 is a perspective view of the device at the time of the detection of arterial blood pressure and is contemporaneous in time with FIG. 4.

Considering the drawings in greater detail, the arterial blood sampling device comprises an outer barrel 10, having an open end 12, and a closed end 14, thrust portion 16 within barrel 10, a needle or annula 18 having a sharpened end or scarf 20 terminating in proximity to the open end 22 of the thrust portion 16 and the open end 12 of the barrel 10. The end 22 is provided with female threads 24 and teeth 26. The shell vial 28 has a rubber stopper 30 in its open end. The stopper 30 has a plurality of sealing rings 32, a thin central diaphragm 33, and a projection 34 thereon having male threads 36. Teeth 38 are also provided at the base of projection 34. The threads 24 and 36 are complementary and are intended to be made up with each other until teeth 38 interlock with teeth 26, whereafter any seizure of the rings 32 on stopper 30 to the walls of vial 28 can be broken. The walls of vial 28 are also provided with an integral annular glass ring 29 in proximity to the open end of the shell vial which serves to limit the outward movement of the stopper 30 from the vial 28. The disk 40 has a central hole 42 therein which serves as a mixing device. Its use is optional. A small amount of an anticoagulant 44 can also be present in the vial prior to the taking of a blood sample. Its use is also optional.

The thumb opening 46 in the side of barrel 10 is intended, by the amount of lateral thumb pressure applied to the outside of vial 28, as shown in FIG. 4, to prevent the outward movement of the vial and its filling with blood under the influence of arterial blood pressure until the nurse or other operator has been satisfied that the device is in an artery, as will be more fully hereinafter explained.

The needle 18 terminates at its other end in chamber 48 which extends from and is affixed to the closed end 14 of outer barrel 10. The chamber 48 has one or more holes 50 in its walls. Concentrically disposed about chamber 48 is outer shell 52 which is also affixed to the closed end 14 of the outer barrel 10. Within the annular space between the outside of chamber 48 and the inside of shell 52 is a thin arterial blood pressure sensitive rubber (or other flexible material) ring 54. The ring 54 normally fits snuggly against the outside of chamber 48 and covers holes 50. There is a slight space between the inside of shell 52 and the outside surface of ring 54 in proximity to holes 50 so that the portion of ring 54 covering holes 50 is free to bulge or flex outwardly under the influence of arterial blood pressure in chamber 48. The ring 54 is of sufficient thickness to be non-responsible to the significantly lower pressure of veinous blood, and hence will not bulge or flex under the influence of veinous blood pressure within chamber 48.

Extending from the free end of chamber 48 is the boss 56 having a hollow central passage 58. A conventional "Luer" lock skirt 60 surrounds boss 56 and is adapted to receive a needle or cannula 62 having a conventional Luer taper 64 and projections 66 which engage and lock with the internal threads 68 in skirt 60.

In operation, the parts as shown in FIG. 1 are first assembled by attaching the needle 62 and making up threads 24 and 36 to cause the scarf 20 of needle 18 to pierce diaphragm 33. Teeth 26 and 38 interlock and the seizure, if any, of the rings 32 of stopper 30 to the walls of vial 28 broken by the application of rotational force to the vial 28. The device is then held with the thumb pressing laterally on vial 28 through thumb opening 46, as shown in FIG. 6. The nurse then attempts to insert the free end of needle 62 in the artery of the patient. When the free end of needle 62 is inserted in an artery while the device is so held, the ring 54 will bulge outwardly under the influence of the pressure of arterial blood, as shown in FIG. 4. This bulge is made more vivid or apparent to the eye due to the pressing of that portion of ring 54 in proximity to the hole 50 against the inner surface of shell 52 creating a ring-like darkened area 53 detectable through shell 52 which is translucent or transparent. It is to be understood that shell 52 need not be present since it is possible to detect such bulging by direct visual observation. The bulging occurs, as will be apparent to those skilled in the art upon examination of the structure shown herein, due to the trapped air in the closed system consisting of the inside of needle 62, chamber 48, needle 18 and vial 28. The ring 54 is of sufficient thickness to be non-responsive to the lower pressure of veinous blood, and consequently, the device provides a fool-proof means of discriminating between the two fundamentally diffferent sources of blood within the human body.

Figure 8:
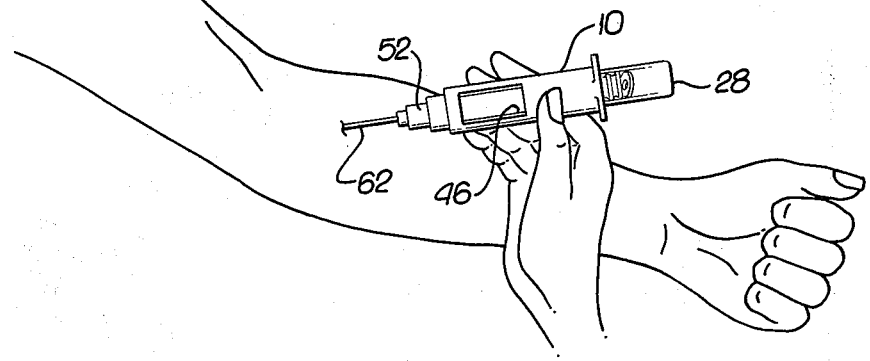
FIG. 8 is a perspective view of the device at a time just prior to the time reflected by FIG. 5, that is, as the device is filling with arterial blood.

The thumb pressure exerted via opening 56 is then released as shown in FIG. 8 and the vial 28 is allowed to move out of the barrel 10, filling with arterial blood as it goes, under the pressure of the arterial blood. This relative movement continues until the outer portion of stopper 30 comes into abutment with the annular ring 29 which serves as a stop and eliminates the necessity for the nurse having to either estimate when the desired volume of arterial blood sample has been taken (the standard desired volume is built-in by the appropriate positioning of annular ring 29 a predetermined distance from the closed end of vial 28 so that the space volume between ring 29 and the closed end of vial 28 approximates the desired volume of the blood sample allowing for the volume of stopper 30 exclusive of projection 24), or watching to see that the vial 28 is not completely pushed out of barrel 10 by arterial blood pressure, dumping the blood on the patient, bed or floor.

It is to be understood that the cannula 62 need not be detachable. It can be permanently affixed. Also, this invention is applicable to conventional syringes to which the arterial blood pressure detecting means has been attached in which case the plunger rather than the vial is manually restrained to cause the evidencing of arterial blood pressure.

Having fully described the invention, it is intended that it be limited solely by the scope of the appended claims.

I claim:

1. A novel and improved arterial blood sampling device comprising:
    an outer barrel having an open end and a closed end,
    a thrust portion disposed within said barrel and having a free end in proximity to the open end of said barrel,
    a vial having an open end and a closed end,
    an imperforate stopper received in said vial,
    means associated with said free end of the thrust portion and said stopper attaching said parts together,
    a fluid path within said thrust portion and terminating in a sharpened end near the free end of the thrust portion and being adapted to pierce said stopper,
    a chamber having side walls extending from the closed end of said barrel and in fluid communication with said fluid path, said side walls containing one or more openings therein,
    a resilient ring surrounding the outside of said chamber and normally sealing on the outside of said openings, and
    a cannula extending from the free end of said chamber and being in fluid communication with the interior thereof, said cannula having a sharpened scarf at its free end for insertion in an artery, said resilient ring bulging outwardly of the outside of said chamber in proximity to said openings under the influence of arterial blood pressure but not under the influence of venous blood pressure.

2. The device of claim 1 wherein said resilient ring is surrounded in spaced-apart relationship by an outer transparent or translucent shell against which said ring abuts when said bulging occurs to form a visually detectable darkened area on said shell.

3. The device of claim 1 wherein said vial has an annular ring in its wall in proximity to the open end of said wall which limits the outward movement of said stopper from said vial as said vial fills with arterial blood.

4. The device of claim 3 wherein said annular ring is disposed a predetermined distance from the closed end of said vial.

5. The device of claim 1 wherein a thumb-receiving opening is provided in the side of said barrel to prevent the vial from moving with respect to said barrel under the influence of arterial blood pressure until said bulging occurs under the influence of arterial blood pressure.

6. The device of claim 1 wherein said stopper and said thrust portion are attached by complementary threads and interlocked by teeth to break any seizure of the stopper to the vial by the application of further rotational force after said threads have been made up.

7. The device of claim 1 wherein said cannula is detachably connected to said chamber.

8. The device of claim 1 wherein said fluid path within said thrust portion is a cannula.

* * * * *